US006187727B1

(12) United States Patent
Pagano et al.

(10) Patent No.: US 6,187,727 B1
(45) Date of Patent: Feb. 13, 2001

(54) FRAGRANCE MATERIALS

(75) Inventors: Alex R. Pagano, Morris Township, NJ (US); Walter C. Frank, Holland, PA (US)

(73) Assignee: Bush Boake Allen, Inc., Montvale, NJ (US)

( * ) Notice: Under 35 U.S.C. 154(b), the term of this patent shall be extended for 0 days.

(21) Appl. No.: 09/351,948

(22) Filed: Jul. 12, 1999

(51) Int. Cl.[7] .............................. C11D 3/50; C11D 9/44; C07C 69/75; A61K 7/46

(52) U.S. Cl. .......................... 510/106; 510/108; 510/119; 510/152; 510/276; 510/367; 510/394; 424/76.1; 424/76.4; 424/401; 44/275; 512/22; 514/844; 560/1

(58) Field of Search .................................... 510/101, 102, 510/106, 107, 108, 276, 119, 152, 367, 394; 512/22; 560/1; 424/76.1, 76.4, 401; 44/275; 514/844

(56) References Cited

U.S. PATENT DOCUMENTS

| | | | | |
|---|---|---|---|---|
| 3,557,223 | * | 1/1971 | Rylander et al. | 568/814 |
| 4,006,218 | | 2/1977 | Sipos | 424/54 |
| 4,091,090 | | 5/1978 | Sipos | 424/45 |
| 4,131,623 | | 12/1978 | Meyers | 568/436 |
| 4,313,855 | * | 2/1982 | Klein et al. | 512/2 |
| 4,701,278 | * | 10/1987 | Fehr | 510/106 |
| 5,104,851 | * | 4/1992 | Fujikura et al. | 512/14 |
| 5,372,995 | * | 12/1994 | Specker et al. | 512/20 |
| 5,531,910 | * | 7/1996 | Severns et al. | 510/102 |
| 5,614,486 | * | 3/1997 | Giersch et al. | 512/21 |
| 5,721,202 | * | 2/1998 | Waite et al. | 510/102 |
| 6,001,789 | * | 12/1999 | Trinh et al. | 510/191 |

FOREIGN PATENT DOCUMENTS

| | | | |
|---|---|---|---|
| 534455 | | 2/1984 | (AU) . |
| 604716 | * | 9/1978 | (CH) . |
| 1240609 | * | 5/1967 | (DE) . |
| 2444837 | * | 4/1975 | (DE) . |
| 0816322 | * | 1/1998 | (EP) . |
| 03059097 | * | 3/1991 | (JP) . |
| 03066637 | * | 3/1991 | (JP) . |
| 07238295 | * | 9/1995 | (JP) . |
| 07238297 | * | 9/1995 | (JP) . |
| 95/04809 | * | 2/1995 | (WO) . |
| 96/41853 | * | 12/1996 | (WO) . |
| 98/07405 | * | 2/1998 | (WO) . |
| 98/41605 | * | 9/1998 | (WO) . |
| 98/58899 | * | 12/1998 | (WO) . |

OTHER PUBLICATIONS

Levene & Marker, *J. Biol. Chem.* vol. 110, pp. 311–321 (1935).

Abiko et al., *Int. Chem Int. Ed. Engl.,* vol. 34, pp. 793–795 (1955).

Dokl. Akad. Nauk. Azerb. SSSR, vol. 22, No. 6, 1966, pp. 18–22, (Translation Provided).

J. Prakt. Chem. 336, 96–109 (1994) Weyerstahl.

*Scent and Fragrances,* Günther Ohloff, Springer–Verlag, 1990, pp. 33 and 34.

Perfumes, Art, Science and Technology, edited by Müller and Lamparsky, Blackie Academic & Professional, 1994, pp. 303–306, and 318–319.

Chem. Abstracts 66, 55084y, 1966.

* cited by examiner

*Primary Examiner*—Lorna M. Douyon
(74) *Attorney, Agent, or Firm*—Gibbons, Del Deo, Dolan, Griffinger & Vecchione

(57) ABSTRACT

The use of 2-methyl-3-cyclohexylpropanol, esters thereof or mixtures thereof as fragrance materials is disclosed. The subject materials possess unique fragrance notes and are cost-effective materials. The esters are novel compounds.

15 Claims, No Drawings

FRAGRANCE MATERIALS

This invention relates to the use of 2-methyl-3-cyclohexylpropanol and esters thereof, particularly the acetate, as perfumery materials.

BACKGROUND OF THE INVENTION

Many compounds have been described in the literature as fragrance materials. As is the case with many classes of compounds having varied utilities, of the many compounds that are known to possess pleasing fragrance notes, only a very small portion are utilized commercially. There are several reasons for this, notably toxicological constraints, environmental considerations, biodegradability, performance, and cost effectiveness. While all of these factors must be carefully weighed in consideration of whether to introduce a new fragrance material, perhaps the most critical are performance and cost. Performance properties include odor activity, notes, and aesthetics; substantivity; and solubility. The cost effectiveness involves manufacture costs and the amount of the compound required to impart fragrance to a consumable product. Of course, the lower the amount of fragrance material required, the higher its cost effectiveness. Many materials have met some of the above-mentioned criteria, yet have not been successful because of cost versus performance.

It must further be borne in mind that, because fragrance materials are by nature utilized in comparatively small quantities, only a very few benefit from the cost efficiency of large-scale production. All of these factors, combined with the tendency in many countries to take a more rigid regulatory position concerning ingredients in consumable products, have acted to hamper the introduction of new fragrance materials in recent years.

There is an on-going need for new fragrance materials that can be readily synthesized from relatively inexpensive raw materials, meet the criteria set forth above, possess unique fragrance notes and, perhaps most importantly, are cost-effective in use. Such materials are provided in accordance with the present invention.

SUMMARY OF THE INVENTION

The invention relates to the use of 2-methyl-3-cyclohexylpropanol, its esters, particularly the acetate and mixtures thereof as fragrance materials.

DETAILED DESCRIPTION OF THE INVENTION

The compounds found to possess attractive fragrance properties in accordance with the present invention are 2-methyl-3-cyclohexylpropanol, and certain of it esters. 2-Methyl-3- cyclohexylpropanol has the structural formula:

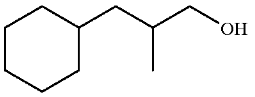

2-methyl-3-cyclohexyl-propanol

2-Methyl-3-cyclohexylpropanol is known in the literature, but there has been to date neither recognition of its fragrant properties nor suggestion that it may possess such properties. 2-Methyl-3-cyclohexylpropyl acetate is a novel compound as are the other esters of 2-methyl-3-cyclohexylpropanol disclosed herein.

2-Methyl-3-cyclohexylpropanol has been disclosed in a series of patents by Sipos assigned to Johnson & Johnson, e.g. U.S. Pat. No 4,091,090 and Australian Patent No. 534,455, as a penetration enhancer and potentiator for topically applied medicaments such as anesthetics and antivirals. The preparation of 2-methyl-3 -cyclohexylpropanol for use in optical relation studies was disclosed by Levene and Marker, J. Biol. Chem. Vol. 110, pages 299–309 (1935). The preparation of 2-methyl-3-cyclohexylpropanol in optically pure form via chiral benzopyranoisoxazolidines has been disclosed by Abiko et al., Chem. Int. Ed. Engl. Vol. 34, pages 793–395 (1995). None of these publications gives any suggestion that 2-methyl-3-cyclohexylpropanol or its ester might possess fragrant properties.

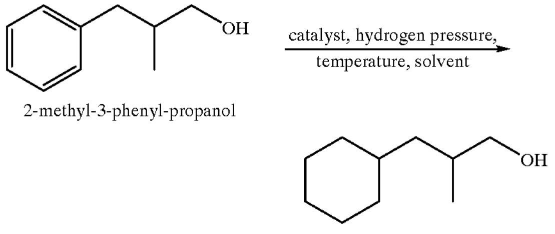

2-methyl-3-phenyl-propanol 2-methyl-3-cyclohexyl-propanol

2-Methyl-3-cyclohexylpropanol is conveniently prepared by hydrogenation of 2-methyl-3-phenylpropanol, a known material that can be conveniently prepared by the hydrogenation of 2-methyl-3-phenyl-1-propen-1-ol, which is commercially available (e.g., from Aldrich Chemical Co.). While 2-Methyl-3-phenylpropanol is the preferred substrate, (α-methyl cinnamaldehyde, or, α-methyl dihydrocinnamaldehyde may also be used as the starting material. Hydrogenation of phenyl rings is well known in the art and the particular method for accomplishing the above transformation is not critical. Those of ordinary skill in the art will readily appreciate that temperature, solvent, catalyst, pressure and mixing rate are all parameters that effect the hydrogenation and how the relationships among them may be adjusted to effect the desired conversion, reaction rate, selectivity, and apparatus limitations.

The above hydrogenation is preferably carried out in a solvent at elevated temperatures and pressures over a suitable active metal hydrogenation catalyst. Acceptable solvents, catalysts, apparatus, and procedures for aromatic hydrogenation can be found in Augustine, Heterogeneous Catalysis for the Synthetic Chemist, Marcel Decker, New York, N.Y. (1996), incorporated herein by reference. Many hydrogenation catalysts are effective, including, without limitation, palladium, platinum, copper chromite, copper, rhodium, ruthenium and the supported versions thereof. Supported catalysts are preferred because the active metal is used more efficiently. Supported nickel is the preferred catalyst. Preferred supports include alumina, silica, carbon, titania, and kieselguhr, with silica and alumina being particularly preferred. While the weight percent of nickel on the support is not critical, it will be appreciated that the higher the metal weight percent the faster the reaction. Generally the nickel weight percent will range from about 5 to about 95%, preferably 25 to 75%, and most preferably 45 to 65%.

The temperature, amount of supported nickel catalyst, and hydrogenation hydrogen pressure are interrelated. The preferred temperature is from about 50° to 500° C., more preferably from about 100° to about 300° C., and most preferred from about 140° to 200° C. According to these temperature parameters, the amount of metal is preferably about 0.01 to 10 weight percent—relative to the weight of the total reaction mixture—preferably 1 to 5%, most preferably 2 to 3% by weight. The hydrogen pressure is preferably about 50 to about 5000 psi, more preferably about 100 to 1000 psi, and most preferably about 200 to 700 psi. Useful solvents include those well known in the art of hydrogenation, such as, hydrocarbons, ethers, and alcohols. Alcohols are most preferred, particularly lower alkanols such as methanol, ethanol, propanol, butanol, and pentanol. Most preferred is to use no added solvent, i.e., the substrate and product alcohols function as solvents.

The esters of 2-methyl-3-cyclohexylpropanol in accordance with the present invention are represented by the following structure:

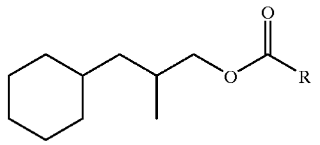

wherein R is a straight- or branched-chain, saturated or unsaturated hydrocarbon radical having from 1 to 24 carbon atoms. Those esters wherein the hydrocarbon radical represented by R contains from 1 to 6 carbon atoms are fragrance materials in accordance with the present invention. Preferred in this group are those esters of the above formula wherein R is a hydrocarbon radical having from 1 to 3 carbon atoms, particularly the acetate. Those esters wherein the hydrocarbon radical represented by R contains from 7 to 24 carbon atoms are also fragrance materials, but are actually sustained release forms of 2-methyl-3-cyclohexylpropanol. Preferred in this group are those esters of the above formula wherein R represents a saturated or unsaturated hydrocarbon radical having 7 to 10, particularly 7 or 8, carbon atoms. Such sustained release fragrances are particularly suited for perfuming a fabric washed with a lipase-containing detergent. In use, the lipase hydrolyzes the ester thereby slowly releasing 2-methyl-3-cyclohexylpropanol onto the fabric.

Another form of ester that likewise acts as a sustained release for 2-methyl-3-cyclohexylpropanol in similar laundry products is a diester represented by the formula $$(C_6H_{11})—CH_2—CH(CH_3)—CH_2—O—C(O)—(CH_2)n—(O)C—O—CH_2—CH(CH3)—CH_2—(C_6H_{11})$$

wherein n is an integer from 0 to 6. Such diesters are hydrolyzed by lipase in the same manner to release 2-methyl-3-cyclohexylpropanol. A particularly preferred diester in accordance with the present invention is bis(2-methyl-3-cyclohexylpropyl) succinate.

The formation of the esters of 2-methyl-3-cyclohexylpropanol is also carried out by conventional reaction with the desired acid anhydride, acid halide, or carboxylic acid, for example, acetic anhydride to form the acetate. Alcohol esterification is a well-known and common synthetic transformation. For example, a list of reagents and methods is presented in Larock, Comprehensive Organic Transformations, VCH Publishers, New York, N.Y. (1989) pp 978–980, incorporated herein by reference. The most preferred reagents, for the purposes of the present invention, are alkyl anhydrides or halides as shown in the following reaction, wherein the alkyl group (R) defines the product ester, with the anhydrides being particularly preferred.

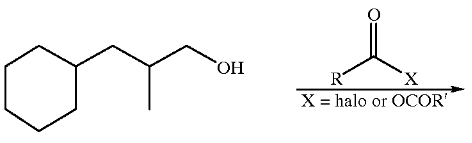

2-methyl-3-cyclohexyl-propanol

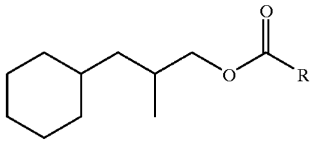

2-methyl-3-cyclohexyl-propanol-ester

The reaction is typically carried out, in a suitable solvent, by adding the alcohol to the anhydride or vise versa. As well known in the art, the temperature is adjusted depending on the reactivity of the anhydride. Cooling, e.g., an ice bath, is generally employed during the exothermic contact of the alcohol with the more reactive anhydrides, whereas higher temperatures are used for the less reactive acid anhydrides or acid halides. In general, the larger the anhydride or halide the less reactive. Those skilled in the art can readily select reaction conditions, which, of course, depend on the esterification agent utilized in a given instance. For example utilizing acetic anhydride, the reaction is performed at 0° C. followed by allowing the reaction mixture to warm to room temperature with stirring for a period of time sufficient to complete the reaction. In addition, catalysts, such as, dimethylaminopyridine and bases like triethyl amine and pyridine may advantageously be used to facilitate the reaction.

2-Methyl-3-cyclohexylpropanol possesses a pleasant green, fruity, rosy fragrance. Lower esters, i.e. those represented by the formula above wherein R contains from 1 to 6 carbon atoms, likewise possess a pleasant fragrance. The acetate, for example, has a very pleasant fruity, rosy fragrance with floral top notes. The unique fragrance notes of the subject compounds make them useful in imparting, augmenting or enhancing the olfactory component in perfume or perfume articles whether that component is intended to impart a characteristic perfume to the article or mask or modify the odor of one or more of the components thereof. Typical household products that can be improved by the use of 2-Methyl-3-cyclohexylpropanol, esters thereof and mixtures thereof include laundry detergent powders and liquids with or without added bleach activators, liquid and powdered cleaners containing chlorine as the active bleaching agent, acid and alkaline household cleaners, toilet soaps, fabric softeners, haircare products, such as shampoos, and air fresheners.

As those skilled in the art will appreciate, fragrant materials are typically utilized in combinations that may include both natural and synthetic ingredients to achieve the desired overall perfume effect. 2-Methyl-3-cyclohexylpropanol and its esters as contemplated herein possess unique fragrant notes and, therefore, are particularly useful individually and in such combinations in perfumes and perfumed articles, such as cosmetics, soaps, air fresheners, candles, various detergent formulations, especially those containing lipase, and other household products. 2-Methyl-3-cyclohexylpropanol and the esters thereof within the present invention may be utilized individually or combined in any proportion and are particularly advantageous in laundry detergent powders and liquids with or without added bleach activators, liquid and powdered cleaners containing chlorine as the active bleaching agent, acid and alkaline household cleaners, toilet soaps, fabric softeners, haircare products, such as shampoos, and air fresheners.

As is conventional in the art, the desired amount of a fragrant material to be added to a given preparation or product is determined by the nature of the product and other factors, such as whether the object is to create a particular fragrance as in a perfume or effectively mask the natural odor of other ingredients in the product to enhance acceptance by the user. The fragrant material is combined with the product in intimate admixture. Typically, where a fragrance component is a combination of a number of fragrance materials, they are combined and formulated to achieve the desired fragrant effect and then admixed with the product. The choice of a carrier, e.g. a solvent or solvent mixture, if any, to be utilized in achieving the desired intimate admixture with the final product is considered to be within the skill of the art. Although greater amounts may be utilized in certain applications, the amount of 2-methyl-3-cyclohexylpropanol, individual esters thereof or mixtures in a perfume or perfumed article in accordance with the present invention will generally not exceed about 1% by weight based on the weight of the final product and can vary from about 0.01% to about 1%, preferably from about 0.02% to about 0.2% weight percent. 2-Methyl-3-cyclohexylpropanol and its esters, particularly the acetate, are particularly advantageous for use as fragrant materials in such preparations because they are cost effective to produce and are projected to be biodegradable.

The following examples further illustrate the invention, but are in no way intended to be limiting thereon.

EXAMPLE 1

Preparation of 2-methyl-3-cyclohexylpropanol.

2-Methyl-3-phenylpropanol (219 g., 1.46 mol.) and 10.30 g. of 50% Ni on silica catalyst (4.7 wt %, G-49-C, United Catalyst) were stirred at 700 rpm in a Parr reactor at 150° C. and 200–600 psi of hydrogen until hydrogen absorption stopped (12 hours). Utilizing 2 wt. % of the catalyst requires that the reaction be run at 180° C. The reaction mixture was filtered through a filter bed (Celite™) using toluene as a rinse solvent and concentrated to a clear, colorless liquid. The odor grade product was isolated by fractional distillation, 174 g., 80% yield; bp 80° C. at 4 mm. Odor: very pleasant green, fruity, rosy. Mass Spectrum from 5508–36. MS (El) m/z (relative intensity) 138 (M+–H2O, 15), 123 (M+–Me and H2O, 15).

EXAMPLE 2

Preparation of 2-methyl-3-cyclohexylpropyl Acetate

To a cooled (0° C.), stirred solution of 2-methyl-3-cyclohexylpropanol (40.3 g., 0.26 mol.), dimethylaminopyridine (2.5 g., 0.02 mol.), and triethylamine (38.4 g., 0.38 mol.) in 200 ml of toluene was added acetic anhydride (39.4 g. 0.39 mol) over 30 minutes. The resulting solution was allowed to warm to room temperature and stirred for an additional 1.5 hours. The reaction mixture was washed twice with 125 ml portions of 2 N aqueous sodium chloride, dried over magnesium sulfate and concentrated to a colorless oil which was distilled to obtain 72 g. 98% yield; bp 67–71° C. at 0.6 mm. Odor: very pleasant fruity, rosy, floral. Mass Spectrum from 5508–36. MS (El) m/z (relative intensity) 155 (M+–C2H3O, 2), 138 (M+–C2H4O2, 15).

We claim:

1. A method of imparting, enhancing or augmenting the fragrance of a perfume or perfumed article comprising adding thereto a fragrance-imparting amount of 2-methyl-3-cyclohexylpropanol, esters thereof represented by the formula $$(C_6H_{11})—CH_2—CH(CH_3)—CH_2—O—C(O)—R$$

wherein R is a straight- or branched-chain, saturated or unsaturated hydrocarbon radical having from 1 to 24 carbon atoms, diesters thereof represented by the formula $$(C_6H11)—CH_2—CH(CH_3)—CH_2—O—C(O)—(CH_2)_n—(O)C—O—CH_2—CH(CH_3)—CH_2—(C_6H_{11})$$

wherein n is an integer from 0 to 6, or mixtures thereof.

2. A method in accordance with claim 1, wherein 2-methyl-3-cyclohexylpropanol is added to said perfume or perfumed article.

3. A method in accordance with claim 1, wherein 2-methyl-3-cyclohexylpropyl acetate is added to said perfume or perfumed article.

4. A method in accordance with claim 1, wherein said article is a laundry detergent powder or liquid.

5. A perfumed article selected from the group consisting of laundry detergent powders, laundry detergent liquids chlorine-containing powdered cleaners, chlorine-containing liquid cleaners, acid household cleaners, alkaline household cleaners, fabric softeners, shampoos, cosmetics, soaps, air fresheners and candles containing as at least a portion of its fragrant component a fragrance-imparting amount of 2-methyl-3-cyclohexylpropanol, esters thereof represented by the formula $$(C_6H_{11})—CH_2—CH(CH_3)—CH_2—O—C(O)—R$$

wherein R is a straight- or branched-chain, saturated or unsaturated hydrocarbon radical having from 1 to 24 carbon atoms, diesters thereof represented by the formula $$(C_6H11)—CH_2—CH(CH_3)—CH_2—O—C(O)—(CH_2)_n—(O)C—O—CH_2—CH(CH_3)—CH_2—(C_6H_{11})$$

wherein n is an integer from 0 to 6, or mixtures thereof.

6. A perfumed article in accordance with claim 5, wherein said article contains a fragrance-imparting amount of 2-methyl-3-cyclohexylpropanol.

7. A perfumed article in accordance with claim 5, wherein said article contains a fragrance-imparting amount of 2-methyl-3-cyclohexylpropyl acetate.

8. A perfumed article in accordance with claim 5, wherein said article is a laundry detergent which contains lipase, which further contains as at least a portion of its fragrant component a fragrance-imparting amount of one or a mixture of an ester represented by the formula $$(C_6H_{11})—CH_2—CH(CH_3)—CH_2—O—C(O)—R$$

wherein R is a straight- or branched-chain, saturated or unsaturated hydrocarbon radical having from 7 to 24 carbon atoms, or a diester represented by the formula $$(C_6H_{11})—CH_2—CH(CH_3)—CH_2—O—C(O)—(CH_2)_n—(O)C—O—CH_2—CH(CH_3)—CH_2—(C_6H_{11})$$

wherein n is an integer from 0 to 6.

9. A perfumed article in accordance with claim 8, wherein the hydrocarbon radical represented by R contains 7 or 8 carbon atoms.

10. A perfumed article in accordance with claim 8 containing a fragrance-imparting amount of bis(2-methyl-3-cyclohexylpropyl)succinate.

11. A perfumed article in accordance with claim 5, wherein said article contains from about 0.01% to about 1% by weight of 2-methyl-3-cyclohexylpropanol, said esters thereof or mixtures thereof.

12. An ester of 2-methyl-3-cyclohexylpropanol selected from esters represented by the formula $$(C_6H_{11})—CH_2—CH(CH_3)—CH_2—O—C(O)—R$$

wherein R is a straight- or branched-chain, saturated or unsaturated hydrocarbon radical having from 1 to 24 carbon atoms, and diesters represented by the formula $$(C_6H_{11})—CH_2—CH(CH_3)—CH_2—O—C(O)—(CH_2)_n—(O)C—O—CH_2—CH(CH_3)—CH_2—(C_6H_{11})$$

wherein n is an integer from 0 to 6.

13. An ester in accordance with claim 12, wherein R contains from 1 to 6 carbon atoms.

14. An ester in accordance with claim 12, wherein R contains from 7 to 24 carbon atoms.

15. A diester in accordance with claim 12, wherein said diester is bis(2-methyl-3-cyclohexylpropyl) succinate.

* * * * *